(12) United States Patent
Bleiel

(10) Patent No.: US 11,103,550 B2
(45) Date of Patent: Aug. 31, 2021

(54) GASTRO-RESISTANT MICROENCAPSULATES, AND USES THEREOF TO STIMULATE IN-VIVO ILEAL GLP-1 RELEASE IN A MAMMAL

(71) Applicant: ANABIO TECHNOLOGIES LIMITED, Dublin (IE)

(72) Inventor: Sinead Bleiel, Dublin (IE)

(73) Assignee: ANABIO TECHNOLOGIES LIMITED, Dublin (IE)

( * ) Notice: Subject to any disclaimer, the term of this patent is extended or adjusted under 35 U.S.C. 154(b) by 0 days.

(21) Appl. No.: 15/536,298

(22) PCT Filed: Dec. 15, 2015

(86) PCT No.: PCT/EP2015/079905
§ 371 (c)(1),
(2) Date: Jun. 15, 2017

(87) PCT Pub. No.: WO2016/096931
PCT Pub. Date: Jun. 23, 2016

(65) Prior Publication Data
US 2019/0022180 A1   Jan. 24, 2019

(30) Foreign Application Priority Data

Dec. 15, 2014  (GB) .................................... 1422259

(51) Int. Cl.
| | | |
|---|---|---|
| *A61K 38/17* | (2006.01) | |
| *A61K 35/20* | (2006.01) | |
| *A23P 10/30* | (2016.01) | |
| *A23L 33/10* | (2016.01) | |
| *A61K 36/48* | (2006.01) | |
| *A61K 31/7016* | (2006.01) | |
| *A61P 3/10* | (2006.01) | |
| *A61K 9/50* | (2006.01) | |
| *A61K 38/16* | (2006.01) | |
| *A23L 33/185* | (2016.01) | |
| *A23L 33/19* | (2016.01) | |
| *A23L 2/52* | (2006.01) | |
| *A61K 9/00* | (2006.01) | |

(52) U.S. Cl.
CPC ............ *A61K 38/1709* (2013.01); *A23L 2/52* (2013.01); *A23L 33/10* (2016.08); *A23L 33/185* (2016.08); *A23L 33/19* (2016.08); *A23P 10/30* (2016.08); *A61K 9/0053* (2013.01); *A61K 9/5052* (2013.01); *A61K 9/5089* (2013.01); *A61K 31/7016* (2013.01); *A61K 35/20* (2013.01); *A61K 36/48* (2013.01); *A61K 38/168* (2013.01); *A23V 2002/00* (2013.01)

(58) Field of Classification Search
CPC .. A61K 38/1709; A61K 36/48; A61K 9/5052; A61K 35/20; A61K 9/5089; A61K 9/0053; A61K 31/7016; A61K 38/168; A23L 2/52; A23L 33/10; A23P 10/30; A23V 2002/00
See application file for complete search history.

(56) References Cited

U.S. PATENT DOCUMENTS

| | | |
|---|---|---|
| 5,536,514 A | 7/1996 | Bishay et al. |
| 5,912,016 A | 6/1999 | Perrier et al. |
| 2008/0213758 A1 | 9/2008 | Hayakawa et al. |
| 2012/0263826 A1 | 10/2012 | Fang et al. |
| 2013/0287928 A1 | 10/2013 | Schweizer et al. |
| 2014/0314944 A1 | 10/2014 | Duvet et al. |
| 2016/0340385 A1 | 11/2016 | Lihme et al. |

FOREIGN PATENT DOCUMENTS

| | | |
|---|---|---|
| CN | 102417599 A | 4/2014 |
| WO | 1992/005708 A1 | 4/1992 |
| WO | 1997/048288 A1 | 12/1997 |
| WO | 2009/053487 A2 | 4/2009 |
| WO | 2010/119041 A2 | 10/2010 |
| WO | 2014/198787 A1 | 12/2014 |

OTHER PUBLICATIONS

Whelehan et al., Microencapsulation using vibrating technology, Journal of Microencapsulation, 2011; 28(8): 669-688. (Year: 2011).*
Singh et al., Microencapsulation: a promising technique for controlled drug delivery, Research in Pharmaceutical Sciences, Oct. 2010; 5(2): 65-77 (Year: 2010).*
Carbonaro et al."Solubility—digestibility relationship of legume proteins." Journal of Agricultural and Food Chemistry 45(9):3387-3394 (1997).
Chavan et al. "Functional properties of protein isolates from beach pea (*Lathyrus maritimus* L.)." Food Chemistry 74 (2):177-187 (2001).
Daniels "US pea protein market 'ready to explode'" (http://www.foodnavigator-usa.com/Markets/US-pea-protein-market-ready-to-explode) pp. 1-5 (2013) (Retreived May 4, 2016).
Feng ""Optimize pH-shifting and ultrasonication to enhance pea protein functionality." https://www.thefreelibrary.com/Optimize+pH-shifting+and+ultrasonication+to+enhance+pea+protein . . . -a0434321260 pp. 1-2 (2015) (Retrieved Jun. 15, 2017)".
Klemmer et al. "Pea protein-based capsules for probiotic and prebiotic delivery." International Journal of Food Science & Technology 46(11):2248-2256 (2011).

(Continued)

*Primary Examiner* — Robert A Wax
*Assistant Examiner* — Nabila G Ebrahim
(74) *Attorney, Agent, or Firm* — Nixon Peabody LLP; David S. Resnick; Nicole D. Kling

(57) ABSTRACT

A cold-gelated mono-nuclear microencapsulate comprises a unitary liquid core encapsulated within a gastro-resistant, ileal-sensitive, polymerized denatured protein membrane shell, wherein the liquid core comprises a GLP-1 release stimulating agent in a substantially solubilised form. The GLP-1 release stimulating agent is a native protein selected from native dairy protein, native vegetable protein or native egg protein.

13 Claims, 10 Drawing Sheets

(56) References Cited

OTHER PUBLICATIONS

Pereira et al. "Legumes seeds protein isolates in the production of ascorbic acid microparticles." Food Research International 42(1):115-121 (2009).

Picot et al., "Production of Multiphase Water-Insoluble Microcapsules for Cell Microencapsulation Using an Emulsification/Spray-drying Technology." Journal of Food Science 68(9):2693-2700 (2003).

Ragab et al. "Fractionation, solubility and functional properties of cowpea (*Vigna unguiculata*) proteins as affected by pH and/or salt concentration." Food Chemistry 84(2):207-212 (2004).

Mession et al., "Thermal Denaturation of Pea Globulins (*Pisum sativum* L.) Molecular Interactions Leading to Heat-Induced Protein Aggregation." Journal of agricultural and food chemistry 61(6):1196-1204 (2013).

Ianchici et al. "The influence of the method of extraction and drying of proteins from pea seeds on their solubility." Journal on Processing and Energy in Agriculture 15(2):87-89 (2011).

\* cited by examiner

A

B

C

D

GASTRO-RESISTANT MICROENCAPSULATES, AND USES THEREOF TO STIMULATE IN-VIVO ILEAL GLP-1 RELEASE IN A MAMMAL

CROSS REFERENCE TO RELATED APPLICATIONS

This application is a 35 U.S.C. § 371 National Phase Entry Application of International Application No. PCT/EP2015/079905 filed Dec. 15, 2015, which designates the U.S. and claims benefit under 35 U.S.C. § 119(a) of European Provisional Application No. 1422259.0 filed Dec. 15, 2014, the contents of which are incorporated herein by reference in their entireties.

BACKGROUND TO THE INVENTION

The worldwide, rapidly increasing prevalence of overweight and obesity has triggered research into food or food products that have therapeutic potential in the management of overweight, obesity, and associated diseases. For example, so-called functional foods containing nutrients that cause larger reductions in food intake than would be expected on the basis of their caloric contents alone. These functional foods may have a role in dieting plans to improve compliance by reducing between-meal hunger, postponing subsequent meal consumption and reducing caloric intake. Recent studies have shown that under normal physiological situations undigested nutrients can reach the ileum, and induce activation of the so-called "ileal brake", a combination of effects influencing digestive process and ingestive behaviour. The relevance of the ileal brake as a potential target for weight management is based on several findings: First, activation of the ileal brake has been shown to reduce food intake and increase satiety levels. Second, surgical procedures that increase exposure of the ileum to nutrients produce weight loss and improved glycemic control. Third, the appetite-reducing effect of chronic Ileal brake activation appears to be maintained over time. Together, this evidence suggests that activation of the ileal brake is an excellent long-term target to achieve sustainable reductions in food intake.

Given this background, obesity represents $21^{st}$ Century problem—perhaps like never before—the thin line between maintaining both energy intake and a healthy lifestyle. Much has been written in both media and science literature about the health consequences of obesity and inactivity. Despite the attention that this public health phenomenon has received, obesity has replaced more traditional problems such as under-nutrition and infectious diseases as a significant cause of ill-health. Acknowledging that there is no a clear treatment for obesity and that no single intervention provides answers for all patients, this presented encapsulation invention tackles this issue with significant health benefits via activation of the ileal brake system.

Activation of the ileal brake is associated with secretion of gut peptides such as peptide YY (PYY) and Glucagon-Like Peptide-1 (GLP-1). GLP-1 is known to reduce food intake and hunger feelings in humans and is assumed to be an important mediator of ileal brake activation. Activation of the ileal brake is associated with secretion of gut peptides such as PYY and GLP-1. GLP-1 is known to reduce food intake and hunger feelings in humans and is assumed to be an important mediator of ileal brake activation. Furthermore, GLP-1 is an incretin derived from the transcription product of the proglucagon gene that contributes to glucose homeostasis. GLP-1 mimetics are currently being used in the treatment of Type 2 diabetes. Recent clinical trials have shown that these treatments not only improve glucose homeostasis but also succeed in inducing weight loss. Increasing endogenous GLP-1 secretion by functional foods can be expected to mimic these effects in obese and overweight subjects, because the pathways involved in GLP-1 secretion and incretin effects are preserved in obese subjects and in patients with Type 2 diabetes.

As outlined, GLP-1, is a hormone that delays gastric emptying and promotes a feeling of satiety. To date, research has demonstrated that treatment with GLP-1 can potentially enhance endogenous secretion of insulin after a meal, resulting in improved glucose homoeostasis and suppressed appetite. As a result, GLP-1-related drugs have gained credibility from food formulators with much fanfare and anticipated potential for the treatment of obesity and Type 2 Diabetes. However, several major obstacles hinder the oral delivery of GLP-1 due to sensitivity to stomach acid and enzymes. Furthermore, GLP-1 production is low in obese and dieting individuals. In other words, GLP-1 requires added protection to succeed as a credible treatment for Type II Diabetes or obesity. Although, GLP-1 treatments are currently available for the treatment for Diabetes Type II; treatments require subcutaneous injection twice daily, which can cause severe nausea in some patients, especially when treatment is initiated. The invasive nature of subcutaneous administration (i.e. injection) can cause patient discomfort and reduced treatment compliance; hence, an oral GLP-1 format would significantly improve patient comfort, reduce primary healthcare costs and reduce the requirement for primary intervention to treat the follow-on diseases of diabetes.

To-date, the vast majority of oral satiety ingredients tested, utilize peptide doses at least 80× greater than equivalent injectable doses. The higher dose quantity being tested in oral formats clearly compensates for significant losses of peptides experienced during oral delivery, which makes viable commercial applications more problematic. This invention seeks to stimulate the natural release of GLP-1 in the gut in reaction to the presence of native dietary protein in the upper intestine. In this way, the costly delivery of satiety ingredients in excessive doses can be avoided.

Lipids contain essential fatty acids, and the addition of lipids to food products in general increases palatability. These properties make lipids an attractive target to develop functional, caloric intake-reducing foods. For lipids to influence hunger and food intake, digestion to fatty acids is an essential step. Several studies in humans have shown that the effect of lipids on food intake can be augmented by altering the type of fatty acids in triacylglycerols: by increasing fatty acid chain length or by increasing the proportion of unsaturated fatty acids within triacylglycerols.

Another approach to increase the effects of lipids on satiety and food intake is by delaying lipolysis. This results in the exposure of more distal parts of the small intestine to fat and fatty acids. Exposure of the ileum to specific nutrietns, including lipids activates the so-called "Ileal brake". This distal ileal feedback mechanism was initially discovered as an inhibition in small intestinal motility and transit after ileal fat exposure. Activation of the ileal brake also has profound effects on satiety and food intake. After ingestion of a regular meal, only a small proportion of the ingested nutrients will reach the ileum. Therefore, the extent to which the ileal brake has a role in regulation of satiety and food intake under physiologic conditions is uncertain. The magnitude of the effect of ileal brake activation on food intake has been most convincingly shown in animal studies using the ileal transposition technique. In this procedure, a small segment of distal ileum is re-sected with preservation of innervation and vasculature. This segment is transpositioned more proximal with anastomoses between duodenum and proximal jejunum. Regular feeding in this model profoundly activates the ileal brake. The ileal transposition procedure results in marked reductions in food intake and body weight. In humans, studies using catheter-assisted ileal fat infusions have also reported reductions in hunger and food intake after ileal fat administration. A dose of 3 g fat, delivered into the ileum, already significantly reduces between-meal hunger. The data from human and animal experiments indicate that foods or food constituents that enable exposure of the ileum to an increased amount of fatty acids have great potential in the regulation of body weight in obese and overweight patients.

Most of the articles published to date describe the delivery of macronutrients to the ileum by "ileal infusion" using a naso-ileal catheter for the studies. For example, Shin et al. (2013) (*Lipids, CHOs, proteins: can all macronutrients put a 'brake' on eating?*, Shin H S, Ingram J R, McGill A T; et al., Physiological Behaviour 2013 Aug. 15.: 114-23.) gives a very comprehensive review on the mechanism and mediators of the activation of the ileal brake.

There is a predominance of evidence for an ileal brake on eating that comes from lipid studies, where direct lipid infusion into the ileum suppresses both hunger and food intake. Outcomes from oral feeding studies are less conclusive with no evidence that 'protected' lipids have been successfully delivered into the ileum in order to trigger the brake. An example of oral feeding studies are the ones related to 'Fabuless' (Olibra)® a "protected" lipid emulsion. According to these studies the effects were attributed to the arrival of the emulsion into the distal ileum and the subsequent stimulation of the ileal brake (Burns A A, Livingstone M B E, Welch R W, Dunne A, Reid C A, Rowland I R (2001). *The effects of yoghurt containing a novel fat emulsion on energy and macronutrient intakes in non-overweight, overweight and obese subjects. Int J Obes* 25, 1487-1496); (Burns A A, Livingstone M B E, Welch R W, Dunne A, Robson P J, Lindmark L et al. (2000). *Short-term effects of yoghurt containing a novel fat emulsion on energy and macronutrient intakes in non-obese subjects. Int J Obes* 24, 1419-1425.); (Burns A A, Livingstone M B E, Welch R W, Dunne A, Rowland I R (2002). *Dose-response effects of a novel fat emulsion (Olibra) on energy and macronutrient intakes up to 36 h post-consumption. Eur J Clin Nutr* 56, 368-377); (Diepvens K, Steijns J, Zuurendonk P, Westerterp-Plantinga M S (2008). *Short-term effects of a novel fat emulsion on appetite and food intake. Physiological Behaviour* 95, 114-117). However, these oral delivery studies neither demonstrated that the lipid emulsions were protected from absorption in the duodenum or jejunum nor that they were indeed delivered into the ileum. Dobson et al. (2002) (*The effect of ileal brake activators on the oral bioavailability of atenolol in man, International Journal of Pharmaceutics*, Clair L. Dobson Stanley S. Davis Sushil Chauhan Robert A. Sparrow Ian R. Wilding Volume 248, Issues 1-2, 6 Nov. 2002, Pages 61-70) describe the complexities of exploiting natural gastrointestinal processes to enhance the oral bioavailability of drugs. For the study they used atenolol as model drug, and oleic acid and the monoglyceride DGM-04 were formulated into modified release capsules (starch or hard gel) that were targeted to the small intestine. Their conclusion was that ileal brake activators can sometimes influence drug behaviour in the gastrointestinal tract (GI) but the exploitation of a natural process to enhance the bioavailability of drugs will not be straightforward.

For regulation of satiety and food intake, sensing and signaling from the gastrointestinal tract is crucial. Human intubation studies and surgical models in animal studies have shown the potential of ileal brake activation in weight management and in treating diabetes. Under physiologic conditions, only a small amount of dietary fat reaches the ileum. Postponing lipolysis and fat absorption is a well-sought-after target in the development of functional foods. Fabuless (DSM Food Specialities, Delft, Netherlands), a vegetable oil emulsion consisting of palm oil and oat oil, has shown some promise in this respect. Diepvens et al., (2007, 2008) (Diepvens K, Steijns J, Zuurendonk P, Westerterp-Plantinga M S (2008). *Short-term effects of a novel fat emulsion on appetite and food intake. Physiological Behaviour* 95, 114 117); (Diepvens K, Soenen S, Steijns J, Arnold M, Westerterp-Plantenga M. *Long-term effects of consumption of a novel fat emulsion in relation to body-weight management. International Journal of Obesity* 2007; 31:942-9) showed that weight management after initial weight loss improved significantly after ingestion of a yogurt containing Fabuless twice daily compared with placebo. However, the mechanism underlying the effect of Fabuless was previously unknown. Knutson et al., (2010) (Knutson L, Koenders D J P C, Fridblom H, Viberg A, Sein A, Lennernäs H. *Gastrointestinal metabolism of a vegetable-oil emulsion in healthy subjects. Am J Clinical Nutrition* 2010; 92:515 24) reported new data on the gastrointestinal behavior of the Fabuless emulsion. During a human intervention study, the authors compared intragastric infusion of yogurt with either the Fabuless emulsion or milk fats on lipid digestion in a crossover design. An inflated balloon prevented passage of luminal contents beyond the proximal jejunum and allowed sampling at regular intervals. The authors observed that the treatment containing the test product yielded significantly higher amounts of fatty acids in the jejunum compared with the control treatment. This was attributed to the formation of needle-shaped fatty acid crystals after the Fabuless treatment, in which the galactolipids from oat oil seem to play a crucial role. Galactolipids have also been shown to delay and reduce lipolysis by sterically hindering the absorption and penetration of pancreatic colipase and lipase into the oil-water interphase in the duodenum. The mechanism proposed by Knutson et al (2010) is that these crystals function as a "slow-release capsule," gradually dissolving while traversing the gastrointestinal tract. This may result in increased exposure of the ileum to fatty acids, thereby activating the ileal brake. The concept that Fabuless indeed activates the ileal brake needs confirmation in human studies. In the study by Diepvens ei al 2010, however, the increase in GLP-1 secretion as a result of the Fabuless treatment was only observed at 180 min after ingestion of the test product. One may argue whether this small increase in GLP-1 secretion can be expected to improve glucose homeostasis and induce weight loss. Knutson et al., 2010 also points to intriguing mechanisms involving gradual release of free fatty acids from lipid crystals, which are formed through the action of galactolipids.

Little data exists on whether carbohydrates or protein may induce the ileal brake and suppress food intake, although there is a lot of evidence that both clearly have GI mediated effects (e.g. Groger et al., 1997-*Ileal carbohydrates inhibit cholinergically stimulated exocrine pancreatic secretion in humans. Int J Pancreatol.* 22: 23-9; Karhunen et al., 2008-*Effect of protein, fat, carbohydrate and fibre on gastrointestinal peptide release in humans. Regul Pept.* 149(1-3):70-8;

Majaars et al., 2008-*Ileal brake: a sensible food target for appetite control. A review. Physiol Behav.* 95: 271-81; Geraedts et al., 2011a, *Mol Nutr Food Res.* 55(3):476-84. 2011b *PLoS One;* 6: e24878). All of them use catheters for the macronutrient delivery. Some studies state that proteins have been shown to be more satiating than carbohydrates, which in turn are more satiating than fats (Westerterp-Plantenga et al., 2003 (Westerterp-Plantenga et al., 2003, *High protein intake sustains weight maintenance after body weight loss in humans*); (Westerterp-Plantenga et al., 2004), (M. S. Westerterp-Plantenga, M. P. Lejeune, I. Nijs, M. van Ooijen, E M. Kovacs., *Journal Obesity Relation Metabolism Disorder.*, 28 (2004), pp. 57-64), Maliaars et al, 2008 (Maljaars J, Symersky T, Kee B C., Haddeman E, Peters H P, et al. (2008) *Effect of ileal fat perfusion on society and hormone release in healthy volunteers. International Journal of Obesity* 32: 1633-1639).

It has been confirmed that glucose sensors are present in both the proximal and the distal GI tract with a feedback loop to inhibition of gastric emptying when glucose was delivered to the ileum. The response was related to the length of the SI exposed to the nutrient (Lin et al 1989). But according to Shin et al. (2013) there are no clinical studies which have investigated the effect of ileal infusion of CHO on appetite related outcomes. In relation to proteins, although there is growing evidence that is the most satiating of the macronutrients and may have a role to play in weight control (Poppitt et al., 1998; Anderson et al., 2004; Weigle et al., 2005).

There are no animal models or clinical settings assessing the role of protein-induced ileal brake on appetite and food intake. The article by Van Avesaat et al. (2014), (*Ileal brake activation: macronutrient-specific effects on eating behavior?* van Avesaat M, Troost F J., Ripken D., Hendriks H F., Masclee A A, *International Journal of Obesity*, 2014) seems to be one of the few (according to them, the only one) with human data on effects of ileal exposure to carbohydrates and proteins on food intake and satiety. Still, this study has been done delivering macronutrients through a catheter.

Van Avesaat et al. (2014) demonstrate that with respect to satiety feelings, only infusion of high-dose protein resulted in a significant decrease in hunger. Infusions of lipids or high-dose carbohydrates did not significantly affect feelings of hunger and satiety. Scientists observed an increase in CKK and GLP-1 plasma levels after protein infusions. And they also observed increase in PYY secretion following lipid and carbohydrate infusion. Apparently, they are the first to demonstrate that ileal infusion of all three macronutrients induces a decrease in food intake and that this effect is dose dependent. It is concluded that an ileal brake-satiating effect leads to a decrease in food intake obtained with small amounts of lipid, protein and carbohydrates. Ileal infusion of equicaloric amounts of these macronutrients modulates food intake, GI peptide release (CCK, GLP-1 or PYY) and feelings of hunger.

To summarise prior art to date, extensive literature exists on the physiology of the ileal brake mechanism: it's activation (dietary macronutrients), it's effects (delayed gastric emptying, decreased peristaltic pressure waves in the intestine, etc) and it's mediators (GI peptides like GLP-1 and PYY). Most of the clinical studies deliver the macronutrient with a catheter, and the ones that use oral feeding are inconclusive due to stomach breakdown of the macronutrients.

WO2009/053487 (Universiteit Maastricht) describes methods for treatment or prevention of obesity, or inducement of satiety, that involve oral delivery of intact pea or wheat protein in a delivery vehicle that is resistant to hydrolysis. Enteric coated capsules and microparticles are described as suitable delivery vehicles. The microparticles are made using 20 g sugar nonpareil particles that are coated with a thin film of intact pea protein (1 g), which is then dried and further coated with an acid-resistant polymer such as EUDRAGIT (7 g). Thus, only about 2-5% (w/w) of the resultant microparticles is intact pea protein, which necessitates the use of a high dosage of microparticles to achieve a clinically effective satiety effect.

It is an object of the invention to overcome at least one of the above-referenced problems.

STATEMENTS OF INVENTION

The invention addresses the problems of the prior art, especially oral delivery of native proteins to the proximal ileum to stimulate ileal GLP-1 release by means of the ileal brake mechanism. The invention addresses these problems by providing cold-gelated mono-nuclear microencapsulates having a liquid core of GLP-1 release stimulating agent encapsulated within a gastro-resistant, ileal-sensitive, denatured protein membrane. The membrane protects the core material (i.e. native protein or disaccharide) during transit through the acidic environment of the stomach, preventing digestion of the active agent contained within the core, and releases the core material when it reaches the ileal environment. In addition, the use of a mono-nuclear core-shell type of encapsulate allows for a greater payload of core material (up to 92% of microencapsulate by weight) compared with the nonpareils of WO2009/053487 that deliver less than 5% of intact protein. In addition, as the microencapsulates of the invention are formed by cold gelation, food grade proteins of dairy or vegetable origin may be employed to generate the gastro-resistant, ileal-sensitive, membrane shell, thus obviating the need for specialized synthetic excipients such as EUDRAGIT. Data is provided below demonstrating that the microencapsules of the invention survive transit through the stomach, release their contents in the ileum, and deliver a high payload of GLP-1 release stimulating agents to the proximal ileum in an active form.

In a first aspect, the invention provides a mono-nuclear microencapsulate comprising a core material encapsulated within a gastro-resistant, ileal sensitive, polymerized denatured protein membrane shell. Typically, the microencapsulate is cold-gelated. Typically the core material is liquid. Typically the core material comprises a GLP-1 release-stimulating agent. Typically the core material is selected from a dairy protein, egg protein, vegetable protein, or disaccharide. Typically, the denatured protein comprises dairy protein or vegetable protein.

In a further aspect, the invention provides a typically cold-gelated, mono-nuclear, microencapsulate comprising a liquid core encapsulated within a gastro-resistant, ileal sensitive, polymerized denatured protein membrane shell, wherein the liquid core comprises a native protein, wherein the polymerized denatured protein membrane shell optionally comprises denatured pea protein or denatured whey-containing dairy protein.

In a further aspect, the invention provides a typically cold-gelated, mono-nuclear, microencapsulate comprising a liquid core encapsulated within a gastro-resistant, deal sensitive, polymerized denatured protein membrane shell, wherein the liquid core comprises a native protein selected from native protein of dairy or vegetable origin, wherein the polymerized denatured protein membrane shell optionally comprises denatured pea protein or denatured whey-containing dairy protein.

In a further aspect, the invention provides a typically cold-gelated, mono-nuclear, microencapsulate comprising a liquid core encapsulated within a gastro-resistant, ileal sensitive, polymerized denatured protein membrane shell, wherein the liquid core comprises a native dairy protein, native pea protein, disaccharide, or any mixture thereof, and wherein the polymerized denatured protein membrane shell optionally comprises denatured pea protein or denatured whey-containing dairy protein.

In a further aspect, the invention provides a typically cold-gelated, mono-nuclear, microencapsulate comprising a liquid core encapsulated within a gastro-resistant, ileal sensitive, polymerized denatured protein membrane shell, wherein the liquid core comprises a 6-8% solution of native whey protein, native casein, native milk protein, native pea protein, disaccharide, or any mixture thereof, and wherein the polymerized denatured protein membrane shell comprises denatured pea protein.

In a further aspect, the invention provides a typically cold-gelated, mono-nuclear, microencapsulate comprising a liquid core encapsulated within a gastro-resistant, ileal sensitive, polymerized denatured protein membrane shell, wherein the liquid core comprises a 6-8% solution of native pea protein, sucrose, or any mixture thereof, and wherein the polymerized denatured protein membrane shell comprises denatured pea protein.

In one embodiment, at least 50% of the microencapsulate comprises the liquid core (w/w). In one embodiment, at least 60% of the microencapsulate comprises the liquid core (w/w). In one embodiment, at least 70% of the microencapsulate comprises the liquid core (w/w). In one embodiment, about 70-95% of the microencapsulate comprises the liquid core (w/w).

Preferably, the liquid core comprises a GLP-1 release stimulating agent. In one embodiment, the GLP-1 release stimulating agent is provided in a substantially solubilised form.

Preferably, the GLP-1 stimulating agent is a native protein. In one embodiment, the native protein is selected from native dairy protein, native vegetable protein, disaccharide, or a mixture thereof. Data is provided below demonstrating that native dairy and vegetable protein, and disaccharide, delivered to the proximal ileum by means of the microencapsulates of the invention, stimulate the release of GLP-1.

Typically, the native dairy protein is selected from casein, whey or a mixture thereof.

Typically, the native vegetable protein is selected from pea protein, wheat protein or rice protein, or any mixture thereof.

Typically, the disaccharide is selected from sucrose or maltose.

Preferably, the unitary liquid core has a GLP-1 stimulating agent concentration of 5-10% (w/v).

Preferably, the unitary liquid core has a GLP-1 stimulating agent concentration of 6-8% (w/v).

Preferably, the protein of the gastro-resistant membrane shell is selected from whey-containing dairy protein or vegetable protein.

Typically, the protein of the gastro-resistant membrane shell is selected from whey protein isolate, whey protein concentrate, milk protein concentrate, or pea protein isolate.

The invention also relates to a composition suitable for oral administration to a mammal comprising a multiplicity of microencapsulates of the invention.

Typically, the composition is selected from a food product, a beverage, a food ingredient, a nutritional supplement, or oral dosage pharmaceutical.

The invention also relates to a microencapsulate of the invention, or a composition of the invention, for use in a method of inducing satiety in a mammal, in which the microencapsulate or composition is administered orally.

The invention also relates to a microencapsulate of the invention, or a composition of the invention, for use in a method of promoting weight loss a mammal, in which the microencapsulate or composition is administered orally.

The invention also relates to a microencapsulate of the invention, or a composition of the invention, for use in a method of treating or preventing obesity a mammal, in which the microencapsulate or composition is administered orally.

The invention also relates to a microencapsulate of the invention, or a composition of the invention, for use in a method of glycemic management in a mammal, in which the microencapsulate or composition is administered orally.

The invention also relates to a microencapsulate of the invention, or a composition of the invention, for use in a method of promoting insulin secretion in a mammal, in which the microencapsulate or composition is administered orally.

The invention also relates to a microencapsulate of the invention, or a composition of the invention, for use in a method of reducing blood sugar levels in a mammal, in which the microencapsulate or composition is administered orally.

The invention also relates to a method of making a mono-nuclear microencapsulate having a liquid core encapsulated within a gastro-resistant polymerized denatured protein membrane shell, which method employs a double nozzle extruder comprising an outer nozzle concentrically formed around an inner nozzle, the method comprising the steps of:
  co-extruding a core-forming solution through the inner nozzle of the double nozzle extruder and a denatured protein solution through the outer nozzle of the double nozzle extruder to form mono-nuclear microdroplets; and
  curing the mono-nuclear microdroplets in an acidic gelling bath.

Preferably, the core forming solution comprises a GLP-1 release stimulating agent. In one embodiment, the GLP-1 release stimulating agent is provided in a substantially solubilised form. In one embodiment, the GLP-1 release stimulating agent comprises native protein or disaccharide. In one embodiment, the GLP-1 release stimulating agent comprises native dairy protein. In one embodiment, the GLP-1 release stimulating agent comprises native egg protein. In one embodiment, the GLP-1 release stimulating agent comprises native vegetable protein. In one embodiment, the native protein in the core-forming solution is solubilized by physical means (i.e. sonication) or chemical means (pH). In one embodiment, the native protein is pea protein, and the solution has a pH of at least 10. In one embodiment, the native protein is milk protein, and the solution has a pH of 7-8. In one embodiment, the solution of native protein has a protein concentration of 6-8% (w/v).

In one embodiment, the native dairy protein is selected from casein, whey or a mixture thereof.

In one embodiment, the native vegetable protein is selected from pea protein, wheat protein or rice protein, or any mixture thereof.

In one embodiment, the disaccharide is selected from sucrose or maltose.

In one embodiment, the core forming solution has a GLP-1 stimulating agent concentration of 5-10% (w/v).

In one embodiment, the core forming solution has a GLP-1 stimulating agent concentration of 6-8% (w/v).

In one embodiment, the core forming solution comprises surfactant. In one embodiment, the core forming solution comprises 0.001 to 0.01% surfactant (v/v).

In one embodiment, the denatured protein solution comprises whey-containing dairy protein or vegetable protein.

In one embodiment, the denatured protein solution comprises whey protein isolate, whey protein concentrate, milk protein concentrate, or pea protein isolate.

In one embodiment, the denatured protein solution has a protein concentration of 4-12% (w/v). When the protein is pea protein, the protein concentration is suitably 7-9%, preferably about 8% (w/v). When the protein is whey protein, the protein concentration is suitably 10-12%, preferably about 11% (w/v). When the protein is milk protein protein, the protein concentration is suitably 4-6%, preferably about 5% (w/v).

Preferably, the denatured protein solution is prepared by heat denaturation at a temperature of 70-90° C. for a period of 30-60 minutes. Preferably, the denatured protein solution is fully denatured.

Typically, the denatured protein solution is rapidly cooled immediately after heat denaturation to prevent immediate gelation of the solution.

Preferably the core-forming solution is treated to remove soluble matter.

Preferably the denatured protein solution is treated to remove soluble matter.

In one embodiment, the core forming solution and denatured protein solution are heated prior to and/or during extrusion. In one embodiment, the solutions are heated to 30-40° C.

BRIEF DESCRIPTION OF THE FIGURES

FIG. 2. Mononuclear microencapsulates after vacuum/drum drying and membrane thinning process.

(FIG. 10A) Micro-encapsulates with a membrane. (FIG. 10B) Microbeads with no membranes. (FIG. 10C) Absorption of native protein (casein or pea protein isolate) was significantly increased and controlled as a result of the microencapsulate encapsulation technique (green column) compared to standard microbead extrusion encapsulation (red column). Red column represents protein encapsulated in protein microbeads relative to protein encapsulated in microencapsulates. Column represents relative absorption in the proximal ileum. Bar represents 20 microns.

DETAILED DESCRIPTION OF THE INVENTION

Figure 1A:
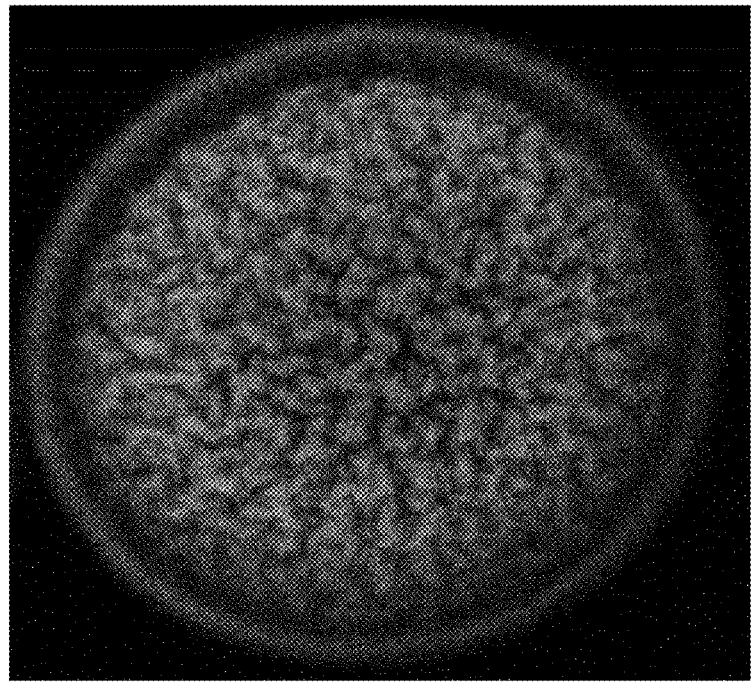
FIG. 1. Light microscopy illustration of mononuclear microencapsulates (A and B) generated using a concentric nozzle for protection of macronutrients.

The present invention utilizes cost-efficient, clean-label, food-grade materials to generate micron-sized capsules for controlled delivery of native protein and/or disaccharide (sucrose) to the proximal ileum for stimulation of the ileal break mechanism and insulin regulation.

This invention outlines the generation of microcapsules with a membrane formulated from a thermal-treated protein source. Depending on the protein source, the protein can be partially or fully denatured. This protein can be sourced from dairy (whey or casein) or vegetable (pea, rice or wheat) ingredients.

In one embodiment, the core of the capsule will contain a GLP-1 release stimulating agent, for example a native protein with vegetable or dairy origin i.e. pea protein, egg protein, whey or casein. It can also contain a disaccharide such sucrose or maltose. Single ingredients or combinations of the aforementioned ingredients (native protein and disaccharides) can also be encapsulated as the core material.

This protein membrane (which is made from thermally treated protein) has proven protection against harsh stomach acid and challenging proteolytic enzymes in the upper intestine. This unique delivery model generates micro-capsules with a gastro-resistant outer membrane that reacts to intestinal conditions and releases the core ingredient(s) at the proximal ileum, the systemic target site.

Data has demonstrated the release of native protein (pea protein or casein) and/or disaccharides (sucrose) at the human proximal ileum, resulting in the production of GLP-1.

The generation of GLP-1 as a result of native protein and/or disaccharide delivery to the proximal ileum, stimulated the Heal break mechanism.

Evidence exists to demonstrate that secreted GLP-1 further triggers the secretion of insulin in pancreatic β-cells.

Definitions

"Cold-gelated": means formed by cold-gelation, in which liquid microdroplets are extruded or sprayed into a gelling bath and immediately cured in a gelling bath due to polymerization of the denatured protein surface film. The bath may be heated or sold. Examples of cold-gelation are described in the literature, for example "Mono-nuclear": as applied to the microencapsulate means that the core material is provided as a single core or nucleus surrounded by a membrane shell, and is different to the microbeads described in the prior art, for example PCT/EP2010/054846 and PCT/EP2014/062154, in which the encapsulated material is provided as a multiplicity of discrete droplets distributed throughout a continuous matrix of encapsulating material. The use of mono-nuclear microencapsulates allows greater amounts of core material to be encapsulated compared to single nozzle microbead formation.

"Microencapsulate": means a mononuclear core/shell type structure having an average dimension in the range of 30-150 microns, preferably 80-120 microns as determined using a method of laser diffractometery (Mastersizer 2000, Stable Micro Systems, Surrey, UK). This method is determines the diameter, mean size distribution and D (v, 0.9) (size at which the cumulative volume reaches 90% of the total volume), of micro-encapsulates with diameters in the range of 0.2-2000 μm. For microencapsulate size analysis, micro-encapsulate batches were re-suspended in Milli-Q water and size distribution is calculated based on the light intensity distribution data of scattered light. Measurement of microencapsulate size is performed at 25° C. and six runs are performed for each replicate batch (Doherty et al., 20111) (Development and characterisation of whey protein microbeads as potential matrices for probiotic protection, S. B. Doherty, V. L. Gee, R. P. Ross, C. Stanton, G. F. Fitzgerald, A. Brodkorb, Food Hydrocolloids Volume 25, Issue 6, August 2011, Pages 1604-1617). Preferably, the microencapsulate is substantially spherical as shown in the attached figures.

"Gastro-resistant": means that the microencapsulates can survive intact for at least 60 minutes in the simulated stomach digestion model described in Minekus et al., 1999 and 2014 (*A computer-controlled system to simulate conditions of the large intestine with peristaltic mixing, water absorption and absorption of fermentation product*, Minekus, M., Smeets-Peeters M, Bernalier A, Marol-Bonnin S, Havenaar R, Alarteau P, Alric M, Fonty G, Huis in't Veld J H, *Applied Microbiology Biotechnology*. 1999 December; 53 (1):108-14) and (Minekus et al., 2014, *A standardised static in vitro digestion method suitable for food an international consensus*, Minekus, A. et al., *Food Function*, 2014, 5, 1113).

"Ileal-sensitive": means that the microencapsulates are capable of releasing their contents in vivo in the ileum of a mammal.

"GLP-1 release stimulating agent" means an agent that is capable of stimulating STC cells to release GLP-1 in an in vitro cell model described below. Preferably, the GLP-1 release stimulating agent is selected from a native protein and a disaccharide. Preferably, the GLP-1 release stimulating agent is selected from a native protein of dairy or vegetable origin. Preferably, the GLP-1 release stimulating agent is pea protein, egg protein, casein, whey protein, disaccharide, or a mixture thereof.

"Native" as applied to protein means that the protein is not denatured, i.e. typically at least 90% and preferably all of the protein by weight is in its native, non-denatured, form. In one embodiment, the native protein is slightly hydrolysed, e.g. up to 20% hydrolysis, by suitable means, e.g. a suitable hydrolyzing enzyme, such that it still functions as a GLP-1 release stimulating agent.

"Native protein of dairy origin": means native whey protein, native casein protein, native milk protein, or a mixture thereof, in any form for example whey protein isolate, whey protein concentrate, caseinate, milk protein concentrate or the like.

"Native protein of vegetable origin": means native pea protein, native wheat protein, native rice protein, in any forms for example as a concentrate or isolate, or proteins derived from other vegetable sources. Preferably, the term means native pea, wheat or rice protein.

"Dairy protein" as applied to the core means casein, whey, or combinations thereof. Typically, the dairy protein is a bovine dairy protein, preferably a dairy protein isolate or concentrate. In one embodiment, the dairy protein is selected from milk protein concentrate, whey protein concentrate, whey protein isolate, and a caseinate, for example sodium caseinate. Typically, the liquid core comprises 6-8% dairy protein, ideally 6.6-7.5% (w/v). Typically the solvent for the dairy protein has a pH of 7-8, ideally about 7.5.

"Vegetable protein": typically means a protein derived from a vegetable or plant, for example pea, wheat or rice, or any combination thereof. The protein may be in the form or a concentrate or an isolate.

"Pea protein" should be understood to mean protein obtained from pea, typically total pea protein. Preferably the pea protein is pea protein isolate (PPI), pea protein concentrate (PPC), or a combination of either. Typically, the liquid core comprises 6-8% pea protein, ideally 6.6-7.5% (w/v). Typically the solvent for the pea protein has a pH of greater than 10 or 10.5. Ideally, the pea protein is solubilised in an alkali solvent.

"Alkali solvent" means an aqueous solution of a suitable base for example NaOH or KOH. Preferably, the alkali solvent comprises an aqueous solution of 0.05-0.2M base, more preferably 0.05-0.15. Ideally, the alkali solvent comprises an aqueous solution of 0.075-0.125 M base. Typically, the alkali solvent is an aqueous solution of NaOH, for example 0.05-0.2M NaOH. Preferably, the alkali solvent comprises an aqueous solution of 0.05-0.2M NaOH or KOH, more preferably 0.05-0.15 NaOH or KOH. Ideally, the alkali solvent comprises an aqueous solution of 0.075-0.125 M NaOH or KOH.

"pH of at least 10" means a pH of greater than 10, typically a pH of 10-13 or 10-12. Ideally, the pH of the pea protein solution is 10.5 to 11.

"Disaccharide" means a sugar molecule comprising two linked saccharide units, for example sucrose, maltose, trehalose or the like. Preferably, the disaccharide is sucrose or maltose.

"Polymerised": as applied to the protein of the membrane shell means that the protein is crosslinked as a result of cold-gelation in a gelling bath. Preferably, the polymerized protein forms a water impermeable shell. Typically, the gelling bath is acidic "Denatured": means partially or fully denatured. Preferably at least 90%, 95% or 99% of the protein is denatured. A method of determining the % of denatured protein is provided below.

"Whey-containing dairy protein" means a whey protein (i.e. whey protein isolate or concentrate) or a milk protein that contains whey (i.e. milk protein concentrate). When the protein is whey, the denatured whey protein solution typically comprises at least 50%, 60% or 70% denatured whey protein. When the protein is milk protein, the denatured milk protein solution typically comprises 4-6%, preferably 5-5.5% denatured milk protein. Preferably, the milk protein is milk protein concentrate.

"Pea protein solution" means a liquid pea protein composition comprising soluble pea protein and optionally insoluble pea protein. The methods of the invention provide for pea protein solutions comprising high levels of soluble pea protein, typically greater than 80%, or 90% (for example, 85-95% soluble pea protein). When the pea protein is mixed with alkali solvent, the amount of soluble pea protein will gradually increase during the resting step until high levels of the pea protein is solubilised in the alkali solvent, at which point the pea protein solution is heat-denatured. This results in a solution of denatured pea protein having very high levels of denatured pea protein present in the form of soluble denatured pea protein aggregates.

The term "soluble" or "solubilised" or "substantially solubilized" as applied to protein, especially protein in the liquid core, should be understood to mean that the protein is present as soluble pea protein aggregates. Typically, the terms mean that the soluble aggregates will not come out of solution upon centrifugation at 10,000×g for 30 minutes at 4° C.

"Resting the native protein solution" means leaving the native protein solution rest for a period of time to allow the native protein to solubilise in the solvent. Generally, the native protein solution is allowed to rest for at least 20, 25, 30, 35, 40, or 45 minutes. Typically, the native protein solution is rested at room temperature. Typically, the native protein solution is rested for a period of time until at least 90% of the native protein has been solubilised.

"Conditions sufficient to heat-denature the protein without causing gelation of the protein solution" means a temperature and time treatment that denatures at least 95% or 99% of the protein present in the solution while maintaining the solution in a form suitable for extrusion (i.e. readily flowable). The temperature and times employed may be varied depending on the concentration of the pea protein solution. Thus, for example, when an 8% pea protein solution (w/v) is used, the solution may be treated at a temperature of 80-90° C. for 20-30 minutes (or preferably 85° C. for 25 minutes). However, it will be appreciated that higher temperatures and shorter times may also be employed.

"Rapidly cooled" means actively cooling the solution to accelerate cooling compared with simply allowing the solution to cool at room temperature which the Applicant has discovered causes the solution to gel. Rapid cooling can be achieved by placing the solution in a fridge or freezer, or on slushed ice, until the temperature of the solution has been reduced to at least room temperature.

"Treated to remove soluble matter" means a separation or clarification step to remove soluble matter such as insoluble protein from the protein solution. In the specific embodiments described herein, centrifugation is employed (10,000×g for 30 minutes at 4° C.) is employed, but other methods will be apparent to the skilled person such as, for example, filtration or the like.

"Solution of denatured protein" means a solution of protein in which at least 90%, 95% or 99% of the total protein is denatured. A method of determining the % of denatured protein in a protein solution is provided below.

"Immediately gelling the droplets in an acidic gelling bath to form microbeads" means that the droplets gel instantaneously upon immersion in the acidic bath. This is important as it ensures that the droplets have a spherical shape and homogenous size distribution. Surprisingly, instantaneuos gelation is achieved by employing an acidic bath having a pH less to the pI of the pea protein, for example a pH of 3.8 to 4.2.

"Acidic gelling bath" means a bath having an acidic pH that is capable of instantaneously gelling the droplets. Typically, the acidic gelling bath has a pH of less than 5, for example 3.5 to 4.2, 3.7 to 4.2, or 3.8 to 4.2. The acidic gelling bath is generally formed from an organic acid. Ideally, the acid is citric acid. Typically, the acidic gelling bath has an acid concentration of 0.1M to 1.0M, preferably 0.3M to 0.7M, and more preferably 0.4M to 0.6M. Typically, the acidic gelling bath has a citric acid concentration of 0.1M to 1.0M, preferably 0.3M to 0.7M, and more preferably 0.4M to 0.6M. Preferably, the acidic gelling bath comprises 0.4 to 0.6M citric acid and has a pH of less than 4.3, typically 3.8 to 4.2.

"Double nozzle extruder" means an apparatus comprising an outer nozzle concentrically arranged around an inner nozzle, and in which the denatured protein solution is extruded through the outer nozzle and the core-forming solution is extruded through the inner nozzle to form microdroplets which are gelled in the gelling bath. Examples of double nozzle extruders include instrumentation provided by BUCHI Labortechnik (www.buchi.com) and GEA NIRO (www.niro.com)

"Cured mono-nuclear microdroplets in the acidic gelling bath" means that the microdroplets are allowed remain in the gelling bath for a period of time sufficient to cure (harden) the microbeads. The period of time varies depending on the microdroplets, but typically a curing time of at least 10, 20, 30, 40 or 50 minutes is employed.

Experimental A: Manufacture of Microcapsules

A: Preparation of Native Protein (Loading Material)
Materials
The following materials have been tested as loading materials in microcapsules:
Whey protein isolate (WPI)
Whey protein concentrate (WPC)
Milk Protein concentrate (MPC)
Sodium caseinate (NaCa)
Pea Protein isolate (PPI)
Sucrose
The core/loading material can be a native protein with vegetable or dairy origin. Disaccharides have also been tested and sucrose appears to be the best candidate for loading.
Method
Prepare a protein dispersion i.e. Suspend 7.0% (w/w), protein basis) in distilled water and disperse under agitation at 4° C. for 24 hours using an overhead stirrer (Heidolph RZR 1, Schwabach, Germany). Prepare a disaccharide dispersion i.e. 7.0% (w/w) in distilled water and disperse under agitation at ambient temperature for 24 hours using an overhead stirrer. When using dairy or vegetable protein sources, HPLC analysis must be performed initially in order to validate the protein and calcium concentration i.e. protein & calcium content will be significantly different between concentrates and isolates. When using milk based proteins (WPI, WPC, MPC or NaCa), adjust solution to pH 7.5 (using 1N/4N NaOH) and add 0.003% Tween 20 in order to encourage the dissolution. When dispersing pea protein (PPI) adjust to pH 10.5 (using 1N/4N NaOH) and add 0.004% tween-80 to enhance protein solubility.

Store solutions at ambient temperature in order to permit full protein hydration.

Centrifuge at 2000×g for 20 minutes at room temperature to remove any undesirable protein agglomerates present form the powder processing. All protein solutions are filtered through 0.45 μm HVLP membranes (Millipore USA) under a pressure of 4 bar using a stainless steel dead-end filtration device. All milk-based protein solutions (WPI, WPC, MPC or NaCa), are sonicated for 90 seconds to remove air pockets formed during filtration. Pea Protein (PPI) is placed under vacuum to remove dissolved air droplets. This process avoids i) blockage of protein in the concentric nozzle and ii) flow discrepancies during encapsulation process which would effect encapsulation efficiency.

B: Preparation of Capsule Material

Materials

Whey protein isolate (WPI)
Whey protein concentrate (WPC)
Milk Protein concentrate (MPC)
Pea Protein isolate (PPI)

Method

Heat-treat the pea protein solution (8.0% w/w) under agitation (200 rpm) at 85° C. and maintain that temperature for a duration of 25 minutes. For MPI, protein concentration must be diluted to 5.2% (w/w,) on a protein basis using phosphate buffered saline (PBS) prior to heat treatment at 78° C. for a duration of 45 minutes. The presence of calcium requires a lower MPI protein concentration to avoid polymerization during heating phase. MPI comprises of β-lactoglobulin and β-casein; hence a more transparent protein dispersion will be generated for use in subsequent encapsulation steps. Heat-treatment of whey protein solutions (WPI, WPC) is performed using the original prepared concentration (11% protein solution, w/w) under agitation (150 rpm) at 78° C. for 45 minutes. Upon completion of the heat treatment step, transfer the protein solutions to crushed ice for immediate cooling. Continue agitation (200 rpm) for 2 hours (room temperature) to prevent further polymerisation of the protein agglomeration. The protein solution in stored overnight (min. 8 hours) at refrigeration temperature. Equilibrate the solution at ambient temperature.

C: Encapsulation Procedure

Mono-nuclear microcapsules were prepared using the co-extrusion laminar jet break-up technique. The encapsulator was fitted with one of two different sized concentric nozzles (internal and external). Heat-treated protein (pea or milk sources) was prepared as outlined above. Heat treated protein dispersions are supplied to the external nozzle using an air pressure regulation system which enabled flow rates of 5-6.6 L/min to be generated using a maximum head pressure of 0.85-1.1 bar. The desired flow rate is set using a pressure reduction valve. The internal phase (native protein, non-heat treated or sucrose) is supplied using a precision syringe pump connected to the inner nozzle to supply the inner phase at flow rates of between 9 and 17.3 L/min. Hence the native material (to be encapsulated; the encapsulant) i.e. casein and/or sucrose is incorporated into the inner core. They can be delivered as a sole protein source or disaccharide source—or they can be blended into a mixture. Spherical microcapsules are obtained by the application of a set vibrational frequency, with defined amplitude, to the co-extruded liquid jet consisting of outer layer of heat-treated protein (pea or milk) material and inner core consisting of native casein and/or sucrose The material in the inner and outer nozzle are both heated to 35° C. in order to allow for better flowability in commercial operations. The resulting concentric jet breaks up into microcapsules, which fall into a magnetically stirred gelling bath 20 cm below the nozzle. The gelling bath consisted of 36 g/l citric acid, 10 mM MOPS, pH 4.0.

Tween-80 is added (0.1-0.2% (v/v)) to reduce the surface tension of the gelation solution. To prevent coalescence of the microcapsules during jet break-up and/or when entering the gelling bath, a high negative charge was induced onto their surface using an electrostatic voltage system which applied an electrical potential of 0-2.15 kV between the nozzle and an electrode, placed directly underneath the nozzle As microcapsules fall through the electrode, they were deflected from their vertical position resulting in their impact occurring over a larger area in the gelation solution Microcapsules were allowed to harden for at least 45 minutes to ensure complete gelation and were then washed and filtered using a porous mesh to remove any un-reacted components.

Experimental B: Characterisation of Microcapules and In-Vitro, Ex-Vivo and In-Vivo Testing Experimental Methods Light Microscopy—Bright-field light microscopy measurements were also carried out using a BX51 light microscope (Olympus, Essex, UK). Samples were deposited on glass slides and analysed on the same day.

Atomic Force Microscopy (AFM)—Atomic Force Microscopy (AFM) images were obtained using Asylum Research MFP-3D-AFM (Asylum Research UK Ltd. Oxford, UK) in AC-mode. Prior to imaging, all samples were diluted (×50, ×100) in MilliQ $H_2O$ and 10 μL aliquots were deposited onto freshly cleaved mica surfaces and subsequently dried in a desiccator. An aluminum reflex coated cantilever with a tetrahedral tip (AC 240), spring constant of 1.8 N/m (Olympus Optical Co. Ltd, Tokyo Japan), working frequency of 50-90 kHz, and scan rate at 1 Hz was used for air-dried samples. The radius of curvature of the tetrahedral tip was 10 (±3) nm.

Confocal Scanning Laser Microscopy (CSLM)—Fluorescent microscopy was performed using a Leica TCS SP5 confocal scanning laser microscope (CSLM) (Leica Microsystems, Wetzler, Germany). Micro-encapsulates were stained using fast green or Thiazole orange (TO) dye for fluorescence of the protein micro-encapsulates. Samples were analysed using ×63 magnification objective with a numerical aperture of 1.4. Confocal illumination was provided by an argon laser (488 nm laser excitation) and red-green-blue images (24 bit), 512×512 pixels, were acquired using a zoom factor of 2.0, giving a final pixel resolution of 0.2 μm/pixel.

Mechanical Strength—The mechanical strength of micro-encapsulates were examined using a texture analyzer (TA-XT2i, Stable Micro Systems, Godalming, UK) as a function of stomach incubation time (0-180 minutes). Briefly, a specific force was applied to a micro-encapsulates monolayer and the quantity of rupture of the micro-encapsulates was assigned as a measure of mechanical stability. A procedure was developed for measurement of mechanical strength and physical integrity of empty and macronutrient-loaded micro-encapsulates with necessary compression conditions acquired from the manufacturer. Strength assays were performed using a 20 mm diameter cylindrical aluminum probe at a mobile speed of 0.3 mm/s in compression mode. A rupture distance of 95% was applied and the peak force (expressed in gram force) exerted by the probe on the micro-encapsulate mono-layer was recorded as a function of compression distance leading to a force vs. incubation time relation. Analysis was conducted on 15 monolayer samples per batch and a total of 10 replicate batches were analysed at each time point to obtain statistically relevant data.

HPLC analysis—Size exclusion chromatography was carried out on FPLC system (AKTA purifier, GE Healthcare) equipped with a Superose 12 10/300 GL column (GE Healthcare Bio-Sciences, Uppsala, Sweden). Pea and Milk protein isolates (100 mg) were dissolved in 1 ml borate buffer (0.1 M sodium borate, 0.2 M sodium chloride, pH 8.3). The proteins were eluted at a flow rate of 0.4 ml per min. The aforementioned buffer was used as mobile phase/eluent. The eluate was continuously monitored at 280 nm. Molecular weight standard kits for gel filtration chromatography (Sigma Aldrich, St. Louis, Mo., USA) were used for calibration.

Capsule Surface hydrophobicity (SH)—SH of whey microencapsulates were determined using the SDS binding method outlined by Kato et al., 1984 (Kato, A., Matsuda, L, Matsudomi, N., & Kobayashi, K. (1984). *Determination of protein hydrophobicity using sodium dodecyl sulfate binding. Journal of Agricultural and Food Chemistry*, 32, 284-288) with particular adjustment for milk and/or pea protein profiles. Protein micro-encapsulates were suspended in sodium dihydrogen phosphate dihydrate buffer (0.02 M; pH 6.0), while SDS reagent (w/v=40.37 mg $L^{-1}$) and methylene blue (w/v=24.0 mg $L^{-1}$) were prepared separately in fresh buffer solutions. Individual micro-encapsulate batches were mixed with SDS reagent (1:2 ratio), incubated for 30 minutes at 20° C. under slight agitation and subsequently dialyzed against the phosphate buffer (v/v, ratio 1:25) for 24 h at 20° C. Mixtures of 0.5 mL of dialysate, 2.5 mL of methylene blue, and 10 mL of chloroform were centrifuged at 2,500×g for 5 minutes. The extinction co-efficient ($\varepsilon$) of the chloroform phase was assessed at a wavelength of $\lambda$=655 nm (according to Hiller and Lorenzen, 2000) (Hiller, B., & Lorenzen, P. C. (2008), *Surface hydrophobicity of physicochemically and enzymatically treated milk proteins in relation to techno functional properties, Journal of Agricultural and Food Chemistry*, 56 (2), 461-468). Measurements were performed in triplicate and SH of fresh microencapsulate batches were assessed relative to batches procured as a function of gastric and intestinal incubation time. Native and heat-treated milk and pea proteins represented positive and negative controls, respectively, and all treatments contained equivalent protein concentration.

SDS-PAGE—The average molecular weights (AMW) of peptides procured during micro-encapsulate digestion in intestinal media were estimated by SDS-PAGE under reducing conditions according to the method described by Laemmli, 1970 (Laemmli, U. K., 1970, *Cleavage of structural proteins during the assembly of the head of bacteriophage T4. Nature*, 227 (5259), 680-685). Treated samples were loaded onto a stacking gel 12% acrylamide and a 4% stacking gel, both containing 0.1% SDS. The running buffer used was free from β-mercaptoethanol due the disassociating effect it has on the protein. This caused the break-up of protein aggregates by reducing intra- and intermolecular disulphide bonds. The electrophoresis was performed at a constant voltage of 180 V in a mini Protean II system (Bio-Rad Alpha Technologies, Dublin, Ireland) and gels were stained in 0.5% Coomassie brilliant blue R-250, 25% iso-propanol, 10% acetic acid solution. The AMW of the protein bands of electrophoretically separated matrix components were estimated by comparison of their mobility to those of standard proteins (Precision Plus Protein™ Standards, Bio-Rad Alpha Technologies).

Size Distribution Analysis—Mean size distribution and D (v, 0.9) (size at which the cumulative volume reaches 90% of the total volume), of micro-encapsulates were determined using a laser diffractometer (Mastersizer 2000, Stable Micro Systems, Surrey, UK) with a range of 0.2-2000 For particle size analysis, micro-encapsulates batches were resuspended Milli-Q water and size distribution was calculated based on the light intensity distribution data of scattered light. Measurement of micro-encapsulate size was performed at 25° C. and three runs were performed for each replicate batch. Micro-encapsulate diameter and size distribution were determined as a function of incubation time, acetate concentration and pH in addition to GI sample analysis.

Micro-encapsulate Digestion—The Degree of hydrolysis (DH) of micro-encapsulates was investigated directly by quantification of cleaved peptide bonds via the o-phthaldialdehyde (OPA) spectrophotometric assay, which involved using N-acetyl-1-cysteine (NAC) as the thiol reagent. To assay proteolysis, 100 µl of each GI sample was added to an equal volume of 24% (w/v) trichloroacetic acid (TCA). Analysis was performed in triplicate for each micro-encapsulate batch obtained. Adler-Nissen, 1979 (*Determination of the degree of hydrolysis of pod protein hydrolysates by trinitrobenzenesulfonic acid*, Adler-Nissen, J., *Journal of Agricultural. Food Chemistry*, 1979, 27 (6), 1256-1262).

Free Amino Acid Analysis—Samples procured from digestion studies were deproteinised by mixing the sample with equal volumes of 24% (w/v) TCA and allowed to stand for 10 min before centrifugation at 14,400×g for 10 minute (Microcentaur, MSE, London, UK). Supernatants were removed and diluted with 0.2M sodium citrate buffer, pH 2.2 to give a final concentration of 125 nM/ml. Amino acids were quantified using a Jeol JLC-500/V amino acid analyzer (Jeol (UK) Ltd., Garden city, Herts, UK) fitted with a Jeol $Na^+$ high performance cation exchange column. Amino acid analysis was performed in triplicate on all GI sample.

Cell Culture—STC-1 cells are maintained in Dulbecco's Modified Eagles Medium (Sigma) with 10% fetal bovine serum (Sigma), 100 units/mL penicillin, and 100 mg/mL streptomycin as additional supplements, at 37° C. in 5% $CO_2$/air humidity. All studies were performed on cells with passage number 30-35.

Digestion/Delivery Testing

In Vitro Studies

In vitro digestion modeling was performed to elucidate the stability and subsequent digestibility of microencapsulates during gut transit. The procedure consists of subjecting (encapsulated and control) treatments to a two-stage digestive process: gastric incubation and intestinal incubation. During in vitro analysis, various factors like digestive enzymes, bile salts, pH, etc. were integrated to simulate transit and digestion of encapsulation systems along the gastrointestinal tract i.e. USP formulation. During the gastric phase, microencapsulates are acidified and a porcine pepsin suspension added under agitation. During the intestinal phase, the pH is neutralised and the mixture incubated at 37° C. in the presence of intestinal enzymes such as trypsin and chymotrypsin under controlled temperature and agitation conditions., Minekus et al., 2014 (*A standardised static in vitro digestion method suitable for food—an international consensus*, Minekus, A. et al., *Food Function*, 2014, 5, 1113).

Ex Vivo Studies

Gastric and intestinal contents from pigs were collected and pooled within 2 hour of slaughter. The starved animals (12 hour prior slaughter) were not prescribed any medicated feed prior to/at the time of collection, gastric and intestinal juices were subject to centrifugation and filtration, and the final suspensions were checked for sterility on brain heart infusion agar (Oxoid Ltd.). Preliminary tests confirmed the absence of indigenous gut microflora within gastric contents; and intestinal contents were screened for relevant background microflora. Standard enzyme assays were performed to validate the enzyme activity and action.

In Vivo Studies (Porcine)

Transit time of microencapsulates along the porcine GI tract was investigated during an in vivo porcine study.

Feeding studies were compliant with European Union Council Directive 91/630/EEC (outlines minimum standards for the protection of pigs) and European Union Council Directive 98/58/EC (concerns the protection of animals kept for farming purposes). Two weeks-post weaning, nine male pigs (Large White×Landrace) were blocked by weight (mean weight of 15.2±0.45 kg) and housed individually in pens designed to provide reasonable space for free movement and normal activity, thereby assuring normal GI motility. All pens equipped with a single feeder and nipple drinker were located in light-controlled (0600 to 1730 h) rooms with temperatures maintained at 28-30 DegreeC throughout the trial using a thermostatically controlled space heater. Day −7 to day 0 represented the acclimatisation period, during which animals were fed a non-medicated commercial diet (free of antimicrobials, performance enhancers, and sweeteners) twice daily at 0730 and 1530 h (350 g/serving) with ad libitum access to fresh water. Pigs were randomly assigned to three groups (n=3), all of which were fasted for 16 h prior to capsule administration microencapsulates, using protein-free milk permeate (MP; Kerry Ingredients, Co. Kerry, Ireland) as the delivery medium. Feeding was staggered by 15 min and as a replacement for their morning feed. Animal variation was kept to a minimum since 1) the relationship between feeding and porcine gastric emptying is influenced by many factors and 2) the rate of emptying can be related to the metabolic requirement of the body. Previous marker transit studies in pigs showed that the majority of ingested feed would have transited to the small intestine within 2 h; however sequential intestinal recovery of microencapsulates may surpass these expectations due to the nature of the delivery system. Hence, sampling was conducted 1 h (n=3), 2 h (n=3) and 3 h (n=3) after administration of microencapsulates Upon ingestion of the capsules, pigs were subsequently sacrificed by captive-bolt stunning followed by exsanguination, in the same order as they were fed. Segments of porcine stomach and intestine (mucosa, duodenum, jejunum, ileum, colonic fluid & tissue) were analysed to verify the absence/presence of microencapsulates.

In Vivo Studies (Human)

A human study was designed whereby four participants were intubated with a 145 cm nasoduodenal catheter. The catheter was introduced into the stomach and the tip was positioned in the intestine under radiological guidance and verification. Following overnight fasting, participants were instructed to consume the encapsulated prototype within 5 minutes (40 mL volume+approx. 120 mL water). After 180-220 min the naso-duodenal catheter was removed and subjects were allowed to eat ad liteum. Position of the catheter is shown on the Table 1.

Results

Encapsulation Efficiency

Figure 1B:
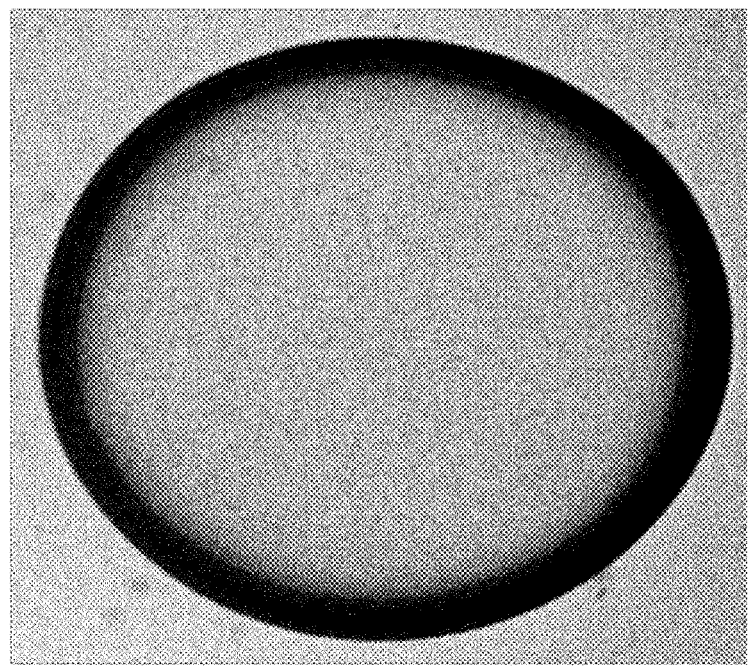

Encapsulation of native macronutrients i.e. casein, native pea protein, sucrose were performed according to the aforementioned method using a concentric nozzle to create a defined core and outer membrane for protection of the encapsulated GLP-1 stimulating ingredient. FIG. 1 illustrates the homogenous mono-nuclear nature of micro-encapsulate batches produced using the presented invention.

Size Distribution & Drying Effects

Figure 2A:
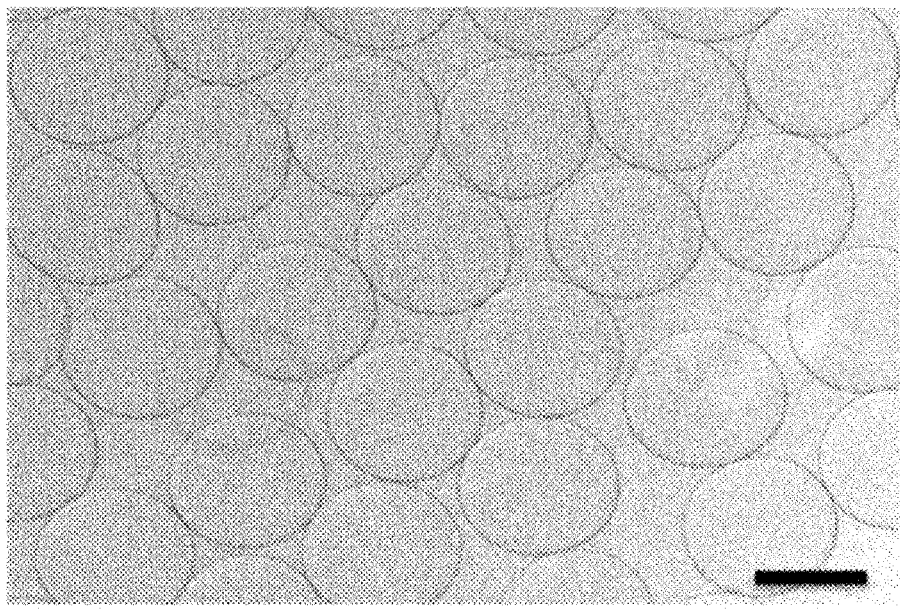
FIG. 2A represents a bar of 100 microns and FIG. 2B illustrates a bar of 40 microns.
Figure 2B:
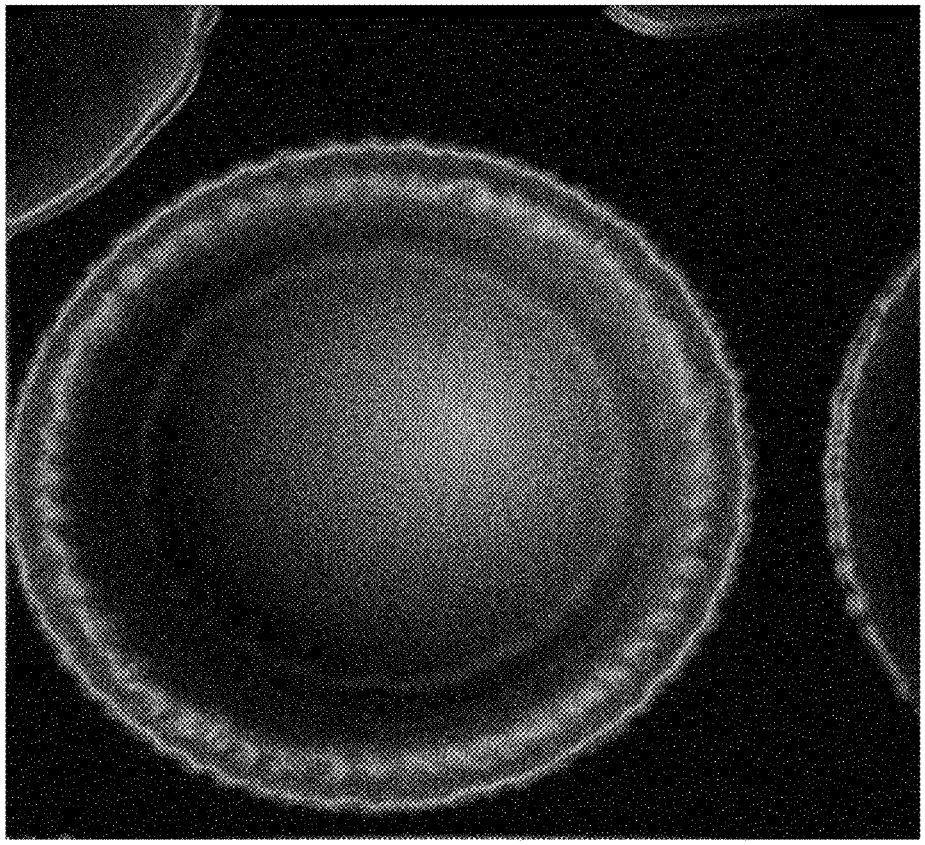

According to light microscopy, micro-beads demonstrated diameters of approx. 200 μm with a narrow range size distribution (+1.2 μm) as shown in FIG. 2. Laser diffractometry was also incorporated and confirmed a D(v, 0.9) values for micro-encapsulates, revealing a diameter of 201.7±0.90 μm and 183.42±0.90 μm, pre- and post-drying respectively. FIG. 2B also visualizes the effect of membrane thinning post drying. The strength of micro-encapsulates significantly increases as a function of drying.

Stomach Incubation & Strength of Micro-Encapsulates

Strength of micro-beads was analyzed as a function of gastric incubation time in vivo (pH 1.2-1.4; 37° C.). No difference in micro-bead strength was reported for stomach incubation and enzyme-activated stomach conditions did not significantly (p, 0.001) weakened micro-bead strength. Tensile strength of micro-encapsulated remained unchanged with no reported leakage or loss of encapsulated casein, pea protein or sucrose. After 180 min gastric incubation, encapsulated casein, pea protein and sucrose microencapsulates maintained high tensile strength 52.03±1.27 nN, 60.31±0.27nN and 58.23±0.12 nN, respectively. Hence, microencapsulates were capable of surviving stomach transit to achieve intestinal delivery.

Figure 3:
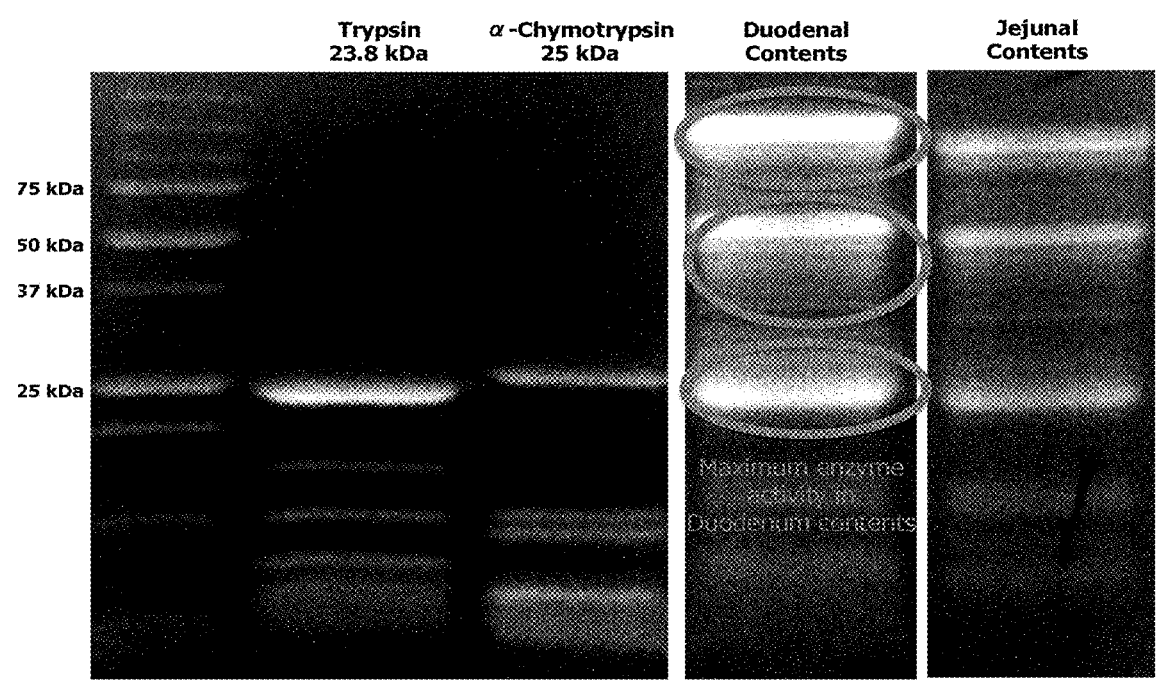
FIG. 3. Identification and characterization of in vivo enzymatic action
Figure 4:
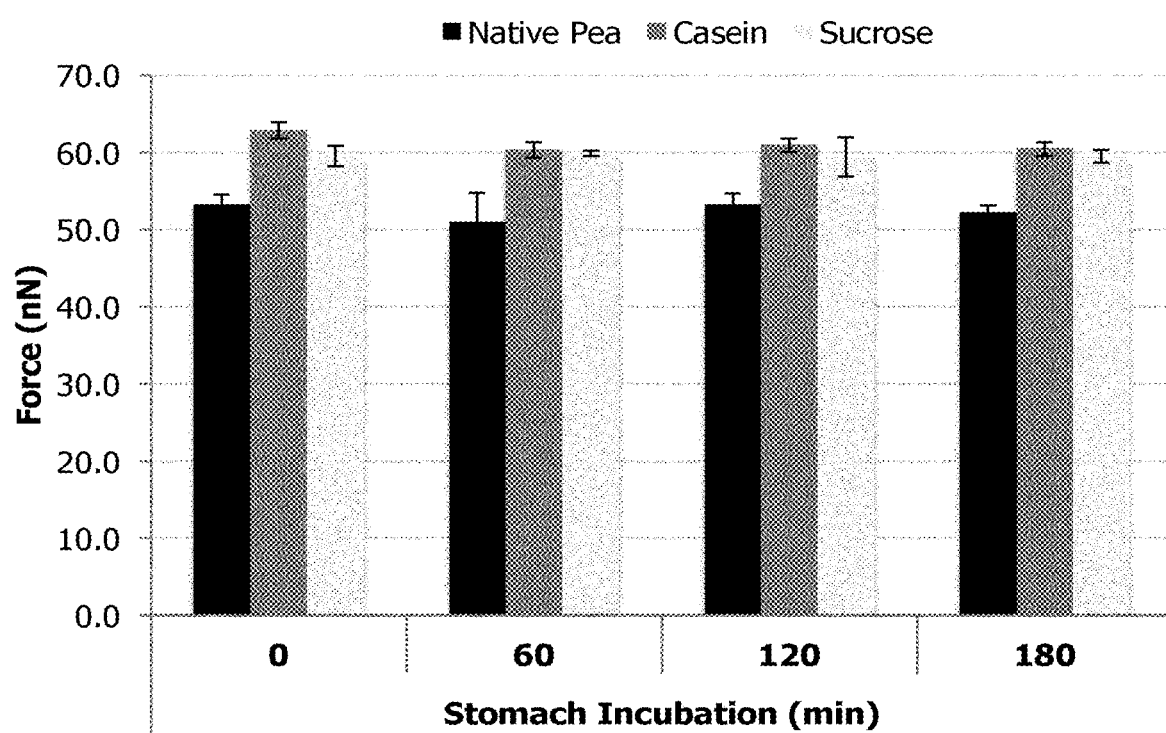
FIG. 4. Effect of in vivo stomach incubation on the tensile strength of microencapsulate with encapsulated pea protein (Black column); casein (dark grey column) and sucrose (light grey column). Data is a average of 12 independent triplicate testings. Image illustrates the integrity maintained of micro-encapsulates after in vivo stomach incubation.

Light microscopy (FIG. 4) validated robust micro-bead integrity after 180 min gastric incubation and did not reveal contractile membranes on the micro-bead periphery after 180 min, a penetrating effect only recognized in pepticactivated capsules. Chromatography (SEC) confirmed the absence of peptides in gastric media after 180 min, and microencapsulates expressed negligible DH; hence, proteolysis was averted during enzyme-activated gastric incubation. Table 1 and FIG. 3 show the identification and characterization of in viva enzymatic action.

TABLE 1

Identification and characterisation of in-vivo enzymatic action

| GI Section | Protein Content (n = 4) | Enzyme Activity (n = 4) | Assay Substrate (n = 4) | μmole Tyrosine equivalent (n = 4) |
|---|---|---|---|---|
| Duodenal Contents | Time 10 min 0.014 mg/mL (±0.00873) | Trypsin | Azo-casein | 21.14 (±1.87) |
| | Time 55 min 0.0098 mg/mL (±0.00119) | Chymo-trypsin | | 319.75 (±21.982) |
| Proximal jejunum/ Ileum | Time 35 min 2.23 mg/mL (±0.00981) | Trypsin | Azo-casein | 2.38 (±0.0321) |
| | Time 120 min 11.76 mg/mL (±0.1382) | Chymo-trypsin | | 89.75 (±11.027) |

Intestinal Incubation

Figure 5:
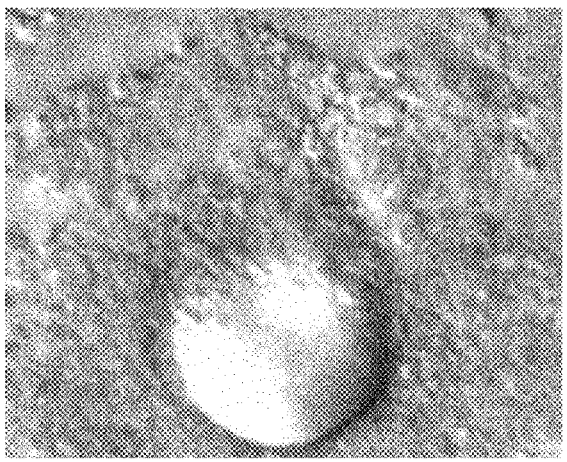
FIG. 5. Microscope images of intact microencapsulates in the human stomach (A and B) and duodenum (C and D) 35 minutes after oral ingestion.
Figure 5:
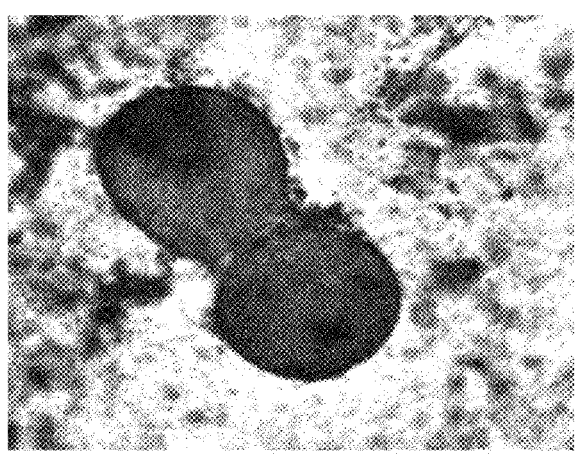
Figure 5:
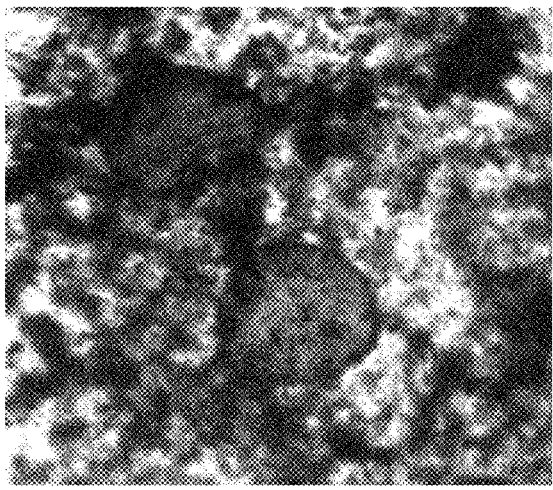
Figure 5:
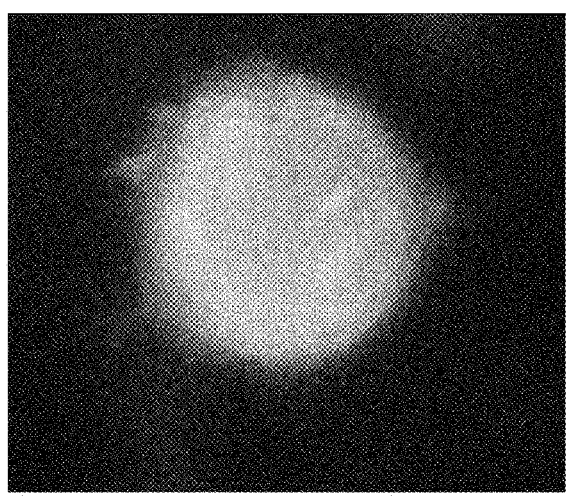

Micro-encapsulates were subsequently tested for intestinal delivery during in vivo transit trials. FIG. 5 illustrates the maintenance of micro-encapsulate integrity in the duodenum 35 minutes after oral ingestion of micro-encapsulates and degradation was not evident.

Ileum Degradation

Figure 6:
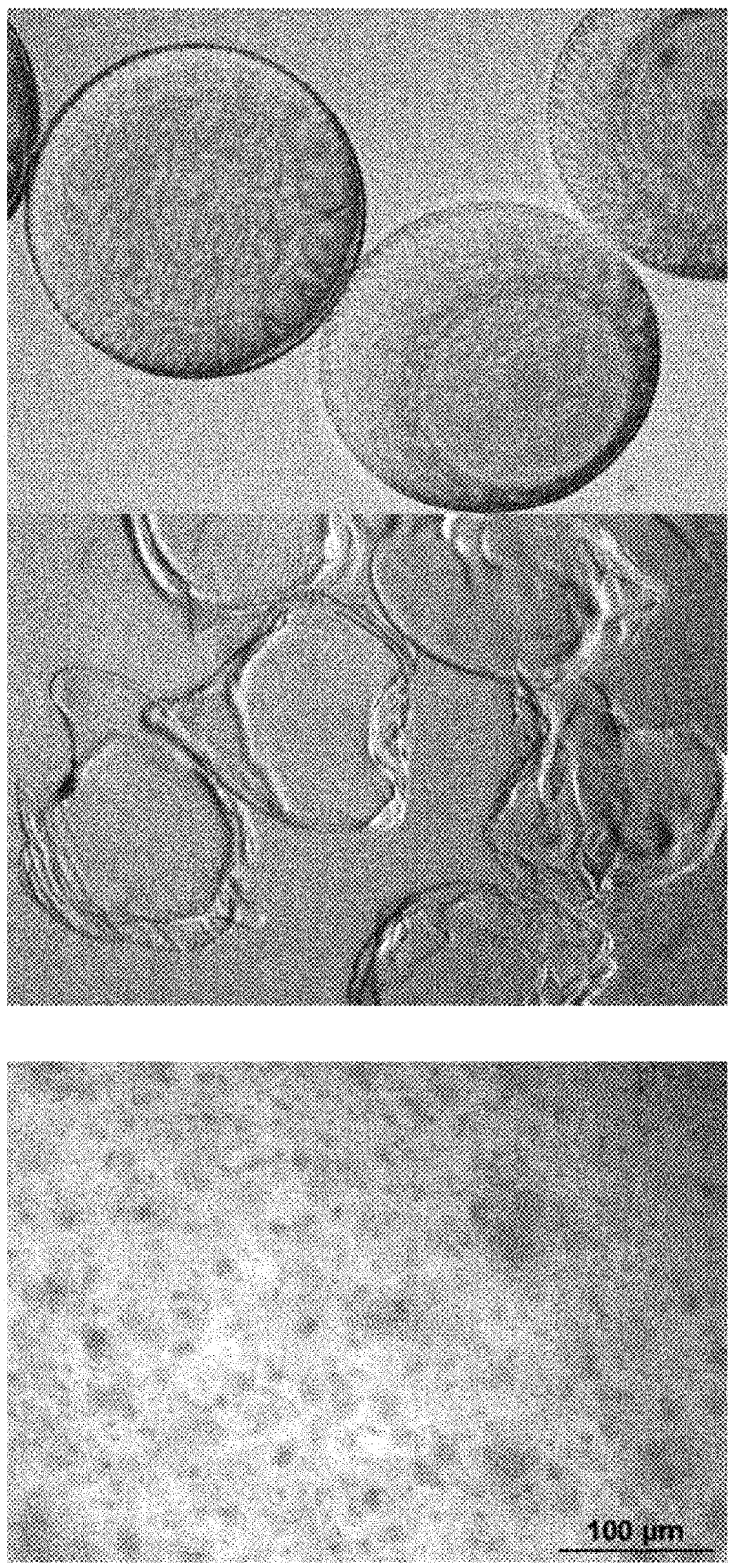
FIG. 6. Microscopic image showing progressive microencapsulate degradation in the human ileum 90 minutes after oral ingestion of encapsulated macro-nutrients. Bars (white) represent 100 microns and (black) 20 microns, respectively.
Figure 7:
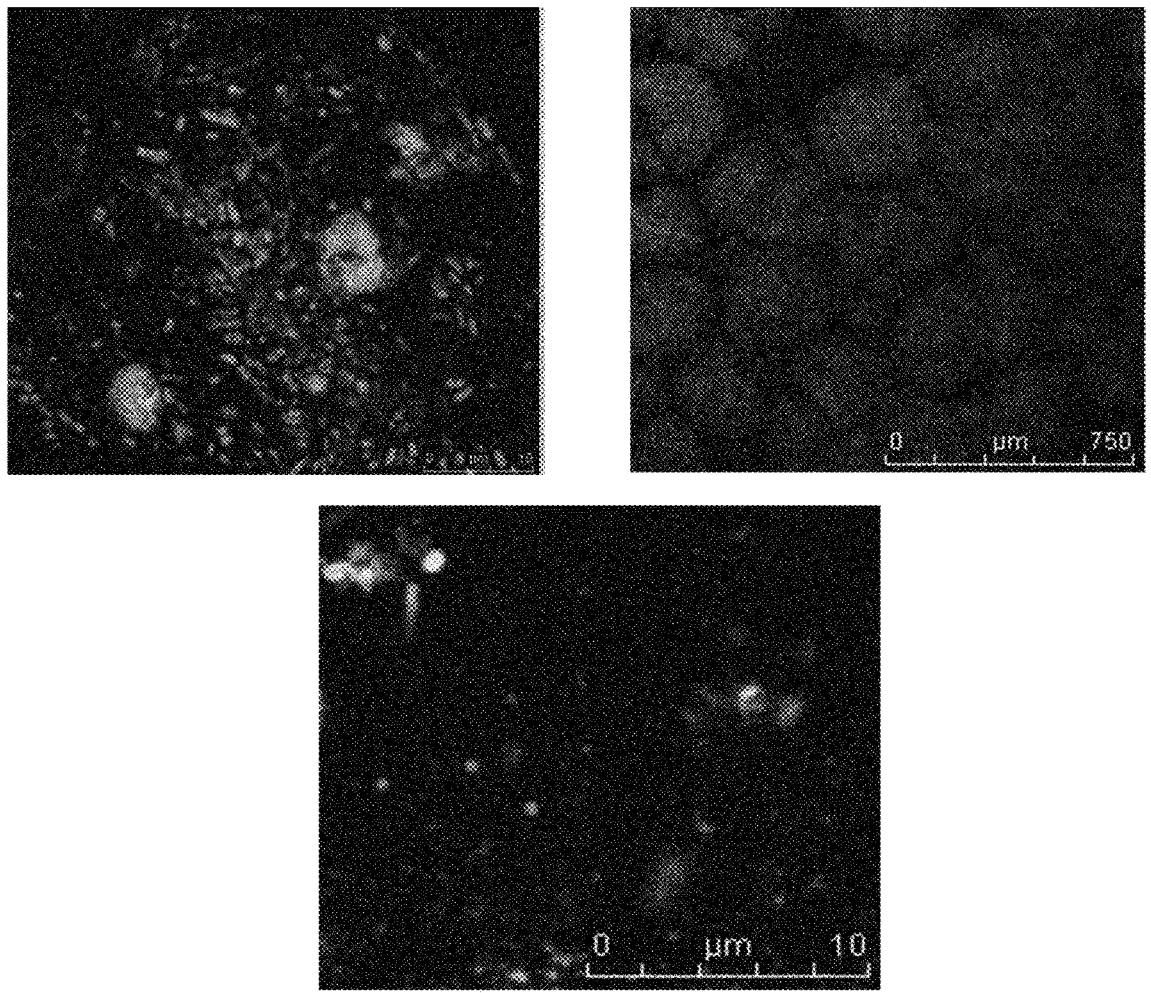
FIG. 7. Confocal imagery of digested microencapsulates in the human ileum 90 minutes after ingestion FIG. 8. Intact native protein (black lines) and peptide release (blue lines) as measured by size exclusion HPLC within the ileum. Trace amounts of peptides identified in the intestinal digesta at T=10 min are represented by the red baseline.

Micro-encapsulate degradation evolved according to expectations during intestinal conditions (in vivo), since protein matrices demonstrated reciprocal sensitivity to pH and enzymatic proteolysis, an imperative pre-requisite for an ileal physiological carrier medium. FIG. 6 illustrates the degradation of microencapsulates as a function of ileum incubation time. As time progressed, the capsulate membrane gradually degrades to release the mononuclear core material.

Liberation of Core Material

Figure 8:
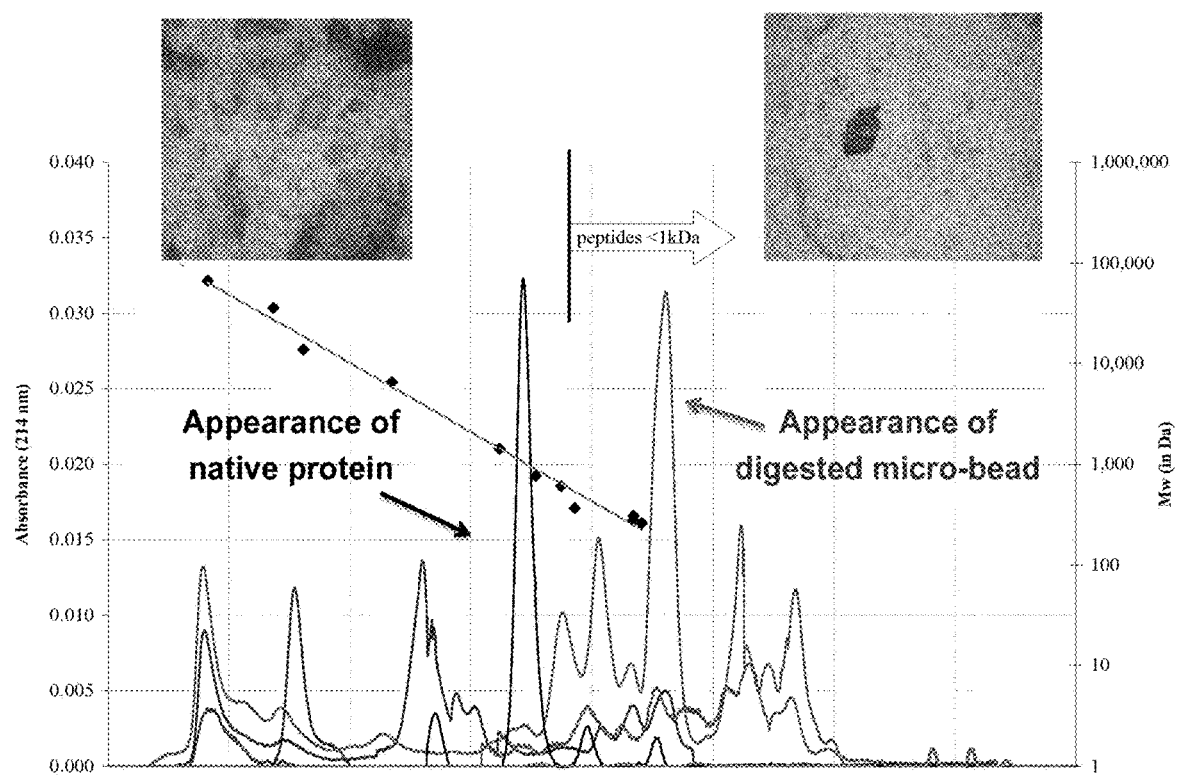
Figure 9:
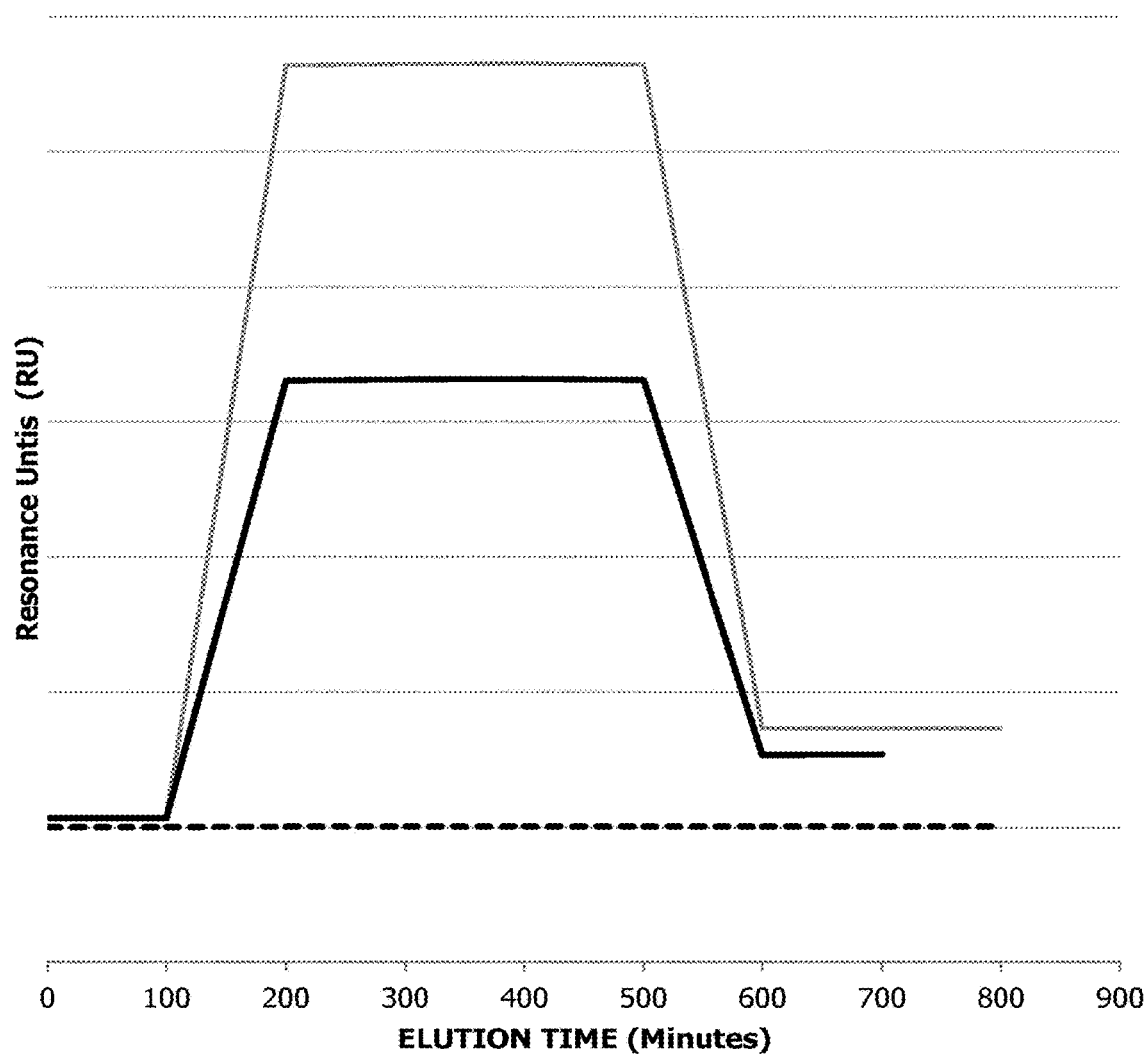
FIG. 9. Data Biacore analysis for detection of sucrose in the jejunum, (black line), in the proximal ileum 90 minutes (blue line) and 120 minutes (red line) after ingestion of microencapsulated sucrose doses. The dose response in the ileum is represented by the blue arrow.

The release of core, GLP-1 stimulating material is identified using methods such as chromatography (FIG. 8), Bradford assay, Surface Plasmon Resonance (FIG. 9) and High pH Anion Exchange Chromatography with Pulsed Amperometric Detection (HPAEC-PAD) to measure sucrose and protein.

Choice of Encapsulation Technology

Figure 10C:
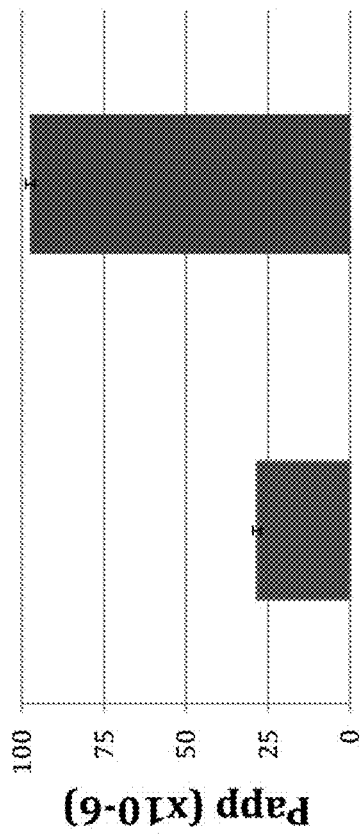
FIG. 10A-10C.
Figure 10B:
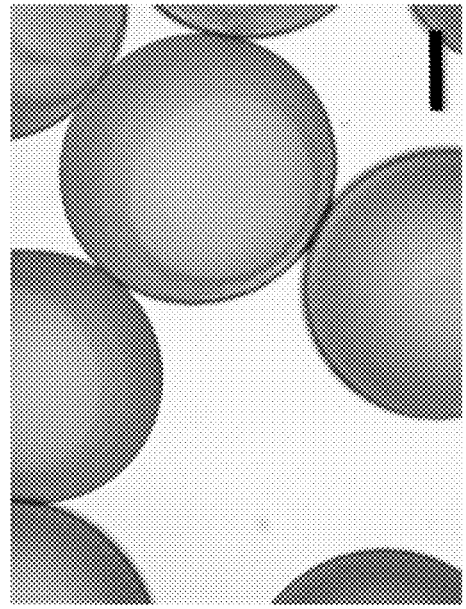
Figure 10A:
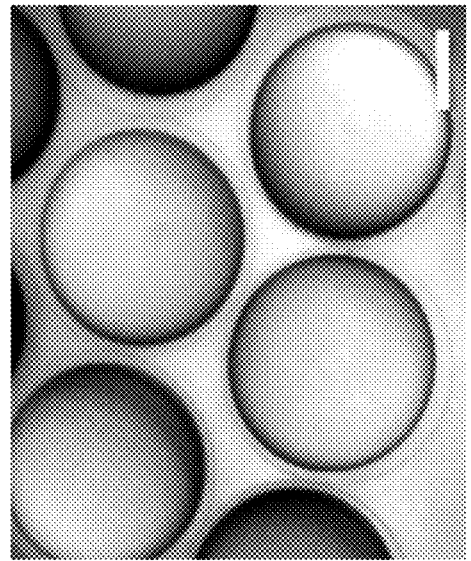

FIG. 10 illustrate the novelty with regard to the microencapsulates with a mononuclear core that can control core release at the ileum. On the contrary, microbeads (FIG. 10B) represent a weak delivery vehicle for native macronutrients, due to the lack of segregation and compartmetnalisation of the native component within the encapsulation structure. FIG. 10A, however, illustrates encapsulates with a defined mononuclear core to enable protection of native macronutrients.

The invention claimed is:

1. A microencapsulate comprising a food-grade core material encapsulated within a food-grade gastro-resistant, ileal-pH and ileal-proteolytic enzyme sensitive membrane shell which is a polymerized denatured protein selected from the group consisting of whey protein isolate, whey protein concentrate, milk protein concentrate and pea protein isolate, wherein the core material is a mono-nuclear liquid core forming at least 50% of the microencapsulate (w/v) and comprises a GLP-1 release stimulating agent selected from the group consisting of native dairy protein, native egg protein, native vegetable protein, or disaccharide, in a solubilised form, wherein the mononuclear microencapsulate does not degrade in the duodenum.

2. The mononuclear microencapsulate of claim 1 wherein the GLP-1 stimulating release agent is native pea protein.

3. The mononuclear microencapsulate of claim 1 wherein the core material has a GLP-1 stimulating agent concentration of 6-8% (w/v).

4. The mononuclear microencapsulate of claim 1 wherein the core material forms 70-95% of the microencapsulate (w/v).

5. The mononuclear microencapsulate of claim 1 wherein the core material comprises surfactant.

6. The mononuclear microencapsulate of claim 1 wherein the core material comprises 7-9% native protein (w/v).

7. The mononuclear microencapsulate of claim 1 wherein the core material comprises disaccharide.

8. A composition suitable for oral administration to a mammal comprising a multiplicity of microencapsulates of claim 1.

9. The composition of claim 8 selected from the group consisting of: a food product, a beverage, a food ingredient, a nutritional supplement, and an oral dose pharmaceutical.

10. A method of inducing satiety, inducing or promoting weight loss, promoting insulin secretion, treating or preventing obesity, or glycemic management in a mammal comprising a step of orally administering to the mammal a mono-nuclear microencapsulate of claim 1.

11. A method of making a mononuclear microencapsulate having a unitary liquid core encapsulated within a gastro-resistant polymerized denatured protein membrane shell wherein the mononuclear microencapsulate does not degrade in the duodenum, which method employs a double nozzle extruder comprising an outer nozzle concentrically formed around an inner nozzle, the method comprising the steps of:

co-extruding a core-forming solution comprising a GLP-1 release stimulating agent through the inner nozzle of a double nozzle extruder and a denatured protein solution through the outer nozzle of the double nozzle extruder to form microdroplets, wherein the core-forming solution and the denatured protein solution is heated to between 30 to 40° C.;

and curing the microdroplets in an acidic gelling bath.

12. The method of claim 11 wherein the core forming solution comprises a GLP-1 release stimulating agent selected from a native dairy protein, a native vegetable protein, a disaccharide, or any mixture thereof, in a solubilised form.

13. The method of claim 11 in which the denatured protein solution is selected from whey protein isolate or whey protein concentrate at a concentration of 10-12% (w/v), milk protein concentrate at a concentration of 4-6% (w/v), or pea protein isolate at a concentration of 7-9% (w/v).

* * * * *